(12) United States Patent
Ehlers et al.

(10) Patent No.: US 11,471,037 B2
(45) Date of Patent: Oct. 18, 2022

(54) PREDICTING CLINICAL PARAMETERS FROM FLUID VOLUMES DETERMINED FROM OCT IMAGING

(71) Applicant: THE CLEVELAND CLINIC FOUNDATION, Cleveland, OH (US)

(72) Inventors: Justis P. Ehlers, Shaker Heights, OH (US); Atsuro Uchida, Beachwood, OH (US); Sunil Srivastava, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 615 days.

(21) Appl. No.: 16/569,434

(22) Filed: Sep. 12, 2019

(65) Prior Publication Data
US 2020/0077883 A1 Mar. 12, 2020

Related U.S. Application Data

(60) Provisional application No. 62/730,140, filed on Sep. 12, 2018.

(51) Int. Cl.
*G06T 7/00* (2017.01)
*A61B 3/00* (2006.01)
(Continued)

(52) U.S. Cl.
CPC ............ *A61B 3/0025* (2013.01); *A61B 3/102* (2013.01); *A61B 5/004* (2013.01); *A61B 5/0066* (2013.01);
(Continued)

(58) Field of Classification Search
CPC ....... A61B 3/0025; A61B 3/102; A61B 5/004; A61B 5/0066; A61B 3/12415; A61B 3/12; A61B 3/14; A61B 5/0073; G06F 17/18; G06N 20/00; G06N 3/02; G06N 3/08–088; G06N 3/0454; G06N 7/00; G06T 7/0012;
(Continued)

(56) References Cited

U.S. PATENT DOCUMENTS 10,169,864 B1 * 1/2019 Bagherinia ............. G06T 7/143
10,251,550 B2 4/2019 Jia et al.
(Continued)

OTHER PUBLICATIONS

Bhende, Muna, et al. "Optical coherence tomography: A guide to interpretation of common macular diseases." Indian journal of ophthalmology 66.1 (2018): 20.
(Continued)

*Primary Examiner* — Jose L Couso
(74) *Attorney, Agent, or Firm* — Tarolli, Sundheim, Covell & Tummino LLP

(57) ABSTRACT

Systems and methods are provided for evaluating an eye using retinal fluid volumes to provide a clinical parameter. An optical coherence tomography (OCT) image of an eye of a patient is obtained. The OCT image is segmented to produce a total retinal volume and one or both of a subretinal fluid volume and an intraretinal fluid volume for a region of interest within the eye. A metric is generated as a function of the total retinal volume and one or both of the subretinal fluid volume and the intraretinal fluid volume. A clinical parameter for the patient is determined from the metric. The determined clinical parameter is provided to a user at a display.

20 Claims, 3 Drawing Sheets

(51) Int. Cl.
 A61B 3/10 (2006.01)
 A61B 5/00 (2006.01)
 G06T 7/11 (2017.01)
 G06F 17/18 (2006.01)
 G06N 20/00 (2019.01)

(52) U.S. Cl.
 CPC ............ *G06F 17/18* (2013.01); *G06N 20/00* (2019.01); *G06T 7/0012* (2013.01); *G06T 7/11* (2017.01); *G06T 2207/30041* (2013.01)

(58) Field of Classification Search
 CPC ............ G06T 7/11; G06T 2207/30041; G06T 2207/10101; G06T 7/12; G06T 7/0016; G06T 7/62; G06T 2207/30101; G06T 2207/30104; G06T 3/4046; G06T 9/002; G06T 2207/20081; G06T 2207/20084; G06K 7/1482; G06K 9/6218; G06K 9/622; G06K 9/6298; G06K 9/6267; G06K 9/6215; G06K 9/628; G06V 10/454; G06V 10/82; G06V 30/18057; G06V 10/762; G06V 30/19107; G06V 10/763; G06V 2201/03; G06V 10/20; G06V 10/245; G06V 10/247; G06V 10/267; G06V 10/44; G06V 10/14; G06V 20/64; G06V 20/69; G06V 40/14; G06V 40/193
 See application file for complete search history.

(56) References Cited

U.S. PATENT DOCUMENTS 10,368,734 B2 * 8/2019 Durbin ................ A61B 3/0025
2011/0034803 A1 * 2/2011 Stetson ................ A61B 3/14
 600/425
2012/0150029 A1 * 6/2012 Debuc ................ A61B 3/102
 600/425
2018/0263490 A1 * 9/2018 Jia ..................... G06T 7/0012
2021/0386285 A1 * 12/2021 Walsh ................ A61B 3/0025

OTHER PUBLICATIONS

Brown, David M., et al. "Intravitreal aflibercept for diabetic macular edema: 100-week results from the VISTA and VIVID studies." Ophthalmology 122.10 (2015): 2044-2052.

Franze, Kristian, et al. "Müller cells are living optical fibers in the vertebrate retina." Proceedings of the National Academy of Sciences 104 20 (2007): 8287-8292.

Itoh, Yuji, Amit Vasanji, and Justis P. Ehlers. "Volumetric ellipsoid zone mapping for enhanced visualisation of outer retinal integrity with optical coherence tomography." British Journal of Ophthalmology 100.3 (2016): 295-299.

Korobelnik, Jean-François, et al. "Intravitreal aflibercept for diabetic macular edema." Ophthalmology 121.11 (2014): 2247-2254.

Marmor, Michael F. "Mechanisms of fluid accumulation in retinal edema." Macular Edema. Springer, Dordrecht, 2000. 35-45.

Murakami, Tomoaki, and Nagahisa Yoshimura. "Structural changes in individual retinal layers in diabetic macular edema." Journal of diabetes research 2013 (2013).

Murakami, Tomoaki, et al. "Foveal cystoid spaces are associated with enlarged foveal avascular zone and microaneurysms in diabetic macular edema." Ophthalmology 118.2 (2011): 359-367.

Samagaio, Gabriela, et al. "Automatic Identification of Macular Edema in Optical Coherence Tomography Images." VISIGRAPP (4: VISAPP). 2018.

* cited by examiner

PREDICTING CLINICAL PARAMETERS FROM FLUID VOLUMES DETERMINED FROM OCT IMAGING

RELATED APPLICATIONS

The present application claims priority to U.S. Provisional Patent Application Ser. No. 62/730,140 filed Sep. 12, 2018 entitled ASSESSMENT METHODS FOR FLUID FEATURE EXTRACTION FOR EVALUATION OF MACULAR EDEMA IN POSTERIOR SEGMENT OPHTHALMIC DISEASES: RETINAL FLUID INDEX (RFI), CYSTIC CIRCULARITY, REFLECTIVITY SIGNATURES, AND CYSTIC ENTROPY MEASURES, the entire contents of which being incorporated herein by reference in its entirety for all purposes.

TECHNICAL FIELD

The present invention relates generally to the field of medical imaging, and more particularly to predicting clinical parameters from fluid volumes determined from optical coherence tomography (OCT) imaging.

BACKGROUND OF THE INVENTION

Diabetic retinopathy (DR) is progressive dysfunction of the retinal microvasculature closely associated with chronic hyperglycemia. It is a leading cause of severe visual impairment among working populations worldwide, affecting one-third of an estimated 422 million individuals with diabetes as of 2014. Diabetic macular edema (DME) remains the most frequent cause of moderate vision loss in eyes with DR, characterized by excessive retinal vascular permeability resulting in accumulation of extra/intracellular fluid and plasma constituents in the neurosensory retina. Population-based studies estimate that up to thirteen percent of patients with diabetes are affected by DME. Similarly, neovascular age-related macular degeneration and other macular vascular disorders are a leading cause of vision loss resulting from the accumulation of retinal fluid due to vascular leakage. There are currently minimal options for characterizing the functional significance of specific fluid features.

SUMMARY OF THE INVENTION

In accordance with an aspect of the present invention, a method is provided for evaluating an eye using retinal fluid volumes to provide a clinical parameter. An optical coherence tomography (OCT) image of an eye of a patient is obtained. The OCT image is segmented to produce a total retinal volume and one or both of a subretinal fluid volume and an intraretinal fluid volume for a region of interest within the eye. A metric is generated as a function of the total retinal volume and one or both of the subretinal fluid volume and the intraretinal fluid volume. A clinical parameter for the patient is determined from the metric. The determined clinical parameter is provided to a user at a display.

In accordance with another aspect of the present invention, a system includes a processor and a non-transitory computer readable medium storing executable instructions executable by the processor. The executable instructions include an imager interface that receives an OCT image of an eye of a patient and a segmentation component that segments the OCT image to produce a total retinal volume and one of an intraretinal volume and a subretinal fluid volume for a region of interest within the eye. A feature extractor generates a metric as a function of the total retinal volume and the one of the intraretinal volume and the subretinal fluid volume. A machine learning model determines at least one clinical parameter for the patient from the metric.

In accordance with yet another aspect of the present invention, a method is provided. A plurality of OCT images of an eye of a patient, with each of the plurality of OCT images being taken at a different time. Each of the plurality of OCT images are segmented to produce each of a total retinal volume, a subretinal fluid volume, and an intraretinal fluid volume for a region of interest within the eye for each of the plurality of OCT images. For each of the plurality of OCT images, a metric is generated as a function of the total retinal volume, the subretinal fluid volume, and the intraretinal fluid volume to provide a set of metrics. At least one clinical parameter is determined for the patient from the set of metrics and provided to a user at a display.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

The development of spectral-domain optical coherence tomography (SD-OCT) has allowed better visualization of retinal microstructures in recent years and provided new insights into the management of DME, AMD and other macular/retinal disorders. Numerous studies have demonstrated the potential utility of examining foveal photoreceptor integrity such as an external limiting membrane (ELM) or ellipsoid zone (EZ, also referred to as IS/OS line) as a surrogate biomarker that correlates with visual acuity in eyes with macular diseases, including DME. However, most studies depended on qualitative assessment or the length of disruption based on several B-scans, and these parameters have not been well validated in the longitudinal follow-up during anti-VEGF therapy. Recent advances in image analysis technology have enabled more advanced assessment of retinal features, including multi-layer retinal segmentation, panmacular EZ integrity mapping, additional retinal bands/ zones, and fluid feature extraction. These assessment platforms provide a unique opportunity to evaluate OCT features in eyes with macular disease in a detailed quantitative fashion and assess potential implications as biomarkers for visual function and disease behavior.

Figure 1:
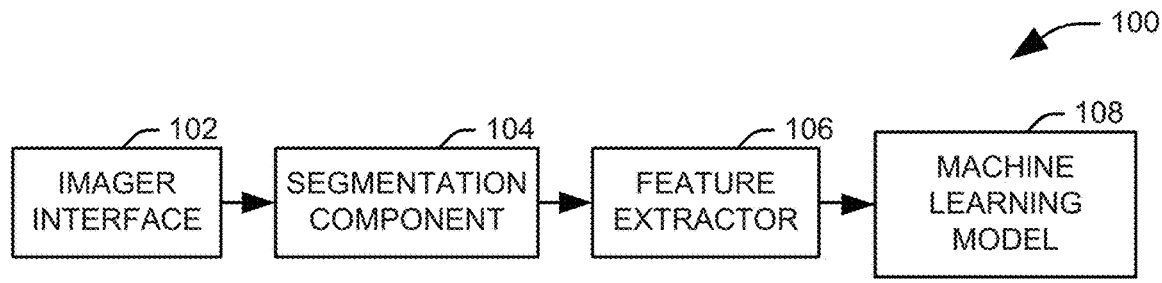
FIG. 1 illustrates a functional block diagram of a system for evaluating an predicting the progression of macular edema in accordance with an aspect of the present invention.

FIG. 1 illustrates a functional block diagram of a system 100 for evaluating an predicting the progression of macular edema in accordance with an aspect of the present invention. It will be appreciated that the system 100 can be implemented as dedicated hardware, machine executable instructions stored on a non-transitory computer readable medium and executed by an associated processor, referred to herein as software, or some combination of dedicated hardware and software components. It will be appreciated that the system 100 can be implemented as a standalone system working in conjunction with an OCT scanner or as an integral part of an OCT scanner.

The system 100 includes an imager interface 102 configured to receive an OCT image of an eye of a patient from an associated scanning assembly. In one implementation, the OCT image is obtained from a SD-OCT imager (not shown). The images are provided to a segmentation component 104 configured to determine a set of boundaries within the image for the internal limiting membrane, the ellipsoid zone (EZ), the RPE band, additional retinal bands/zones, any intraretinal fluid (IRF) and any subretinal fluid. It will be appreciated that this segmentation can be performed using any appropriate automated or semi-automated segmentation algorithm.

A feature extractor 106 processes the segmented image to provide at least one feature representing the patient's eye. In accordance with an aspect of the present invention, the at least one feature includes a feature calculated as a total retinal volume and either or both of a volume of intraretinal fluid or a volume of subretinal fluid within a region of interest within the eye. A machine learning model 108 determines at least one clinical parameter for the patient from the metric. It will be appreciated that the clinical parameter can represent the presence or progression of a retinal disorder, a predicted or actual response to a clinical intervention, an intervention most likely to be successful, a visual acuity of the patient, an expected or actual change in the visual acuity of a patient, an expected progression or development of a retinal disorder, or a likelihood representing any of the categorical parameters listed above.

Figure 2:
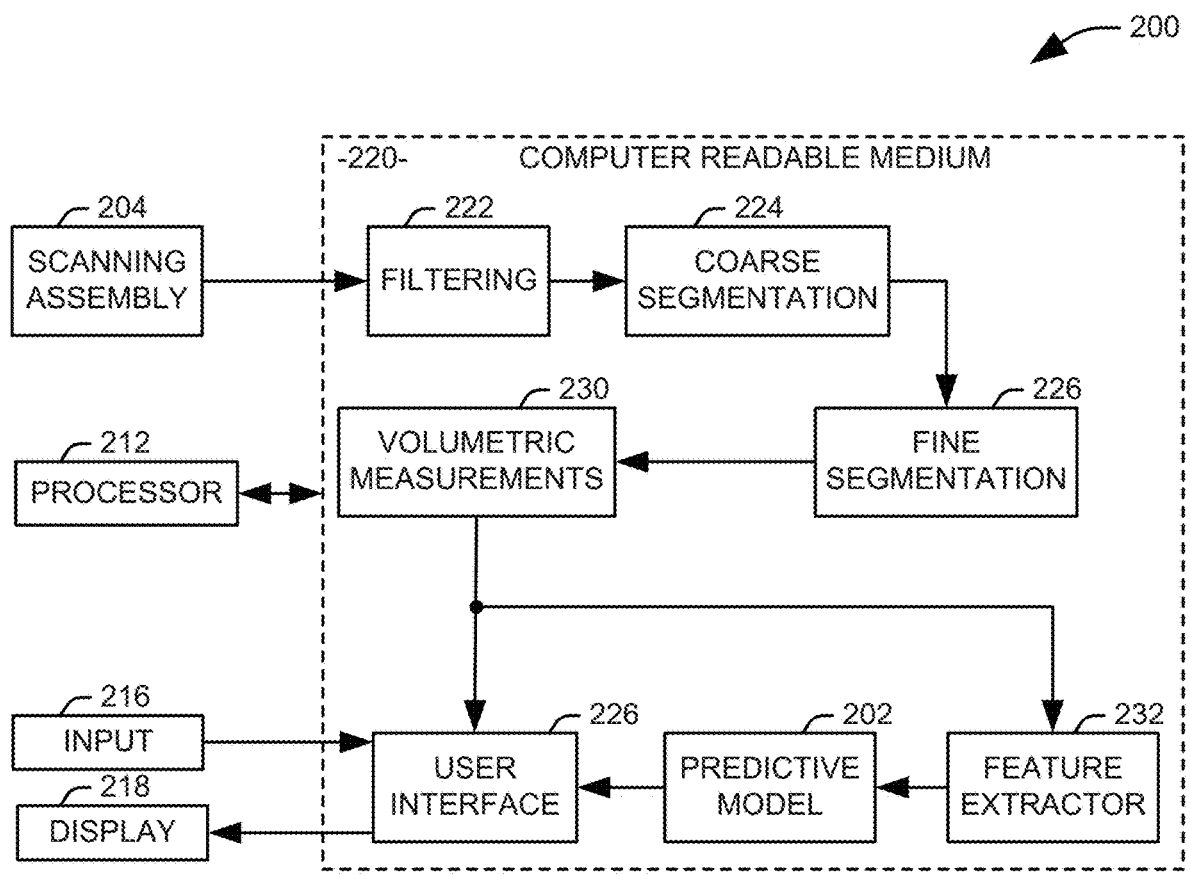
FIG. 2 illustrates one implementation of a system for evaluating an eye using retinal fluid volumes to provide a clinical parameter.

FIG. 2 illustrates one implementation of a system 200 for evaluating an eye using retinal fluid volumes to provide a clinical parameter. To this end, the system 200 incorporates a machine learning model 202 that utilizes features generated from retinal fluid volumes to generate a categorical or continuous clinical parameter representing a diagnosis, a prognosis, or a response to treatment for the patient. In the illustrated implementation, an SD OCT scanning assembly 204 provides OCT B-scan data to an image analysis component 210 implemented as a general purpose processor 212 operatively connected to a non-transitory computer readable medium 220 storing machine executable instructions. An input device 216, such as a mouse or a keyboard, is provided to allow a user to interact with the system, and a display 218 is provided to display imaging data and calculated parameters to the user.

In the illustrated implementation, the machine executable instructions include a filtering component 222 that conditions the received B-scan images for further analysis. In one implementation, image smoothing is performed at the filtering component using a Gaussian convolution window to attenuate noise. A coarse segmentation component 224 performs an automated delineation of a set of constraint boundaries for each image based on natural contours of the retinal, choroidal, or anterior segment topology. Selection of the contours used is dependent on the field of view within the eye. These boundaries serve to constrain the search window, set natural limits on the spatial extent of regions of edema, normalize the image for variations in patient anatomy including shape, curvature, and size, and provide landmarks for volumetric analysis of the regions of edema. For example, contour boundaries can be delineated by local image intensity, gradient, and contrast cues that are determined from immediate pixel neighbors and local regional properties. A user can provide, via the input device 216, an operator-assisted determination of constraint boundaries in the event of an automated boundary detection failure or if it is desirable to select a specific region of interest. Once the constraint boundaries are determined, the coarse segmentation component 224 truncates the image to remove the image area outside of the constraint boundary, decreasing the computation time of subsequent segmentation routines.

In the illustrated implementation, the segmentation of fluid volumes is performed at a fine segmentation component 226. In the illustrated implementation, the fine segmentation component 226 generates an undirected graph with vertices representing image pixels and eight-connected edges having weights representing a cost generated from image gradient and neighborhood similarity metrics, which forms an energy minimization problem based on the costs of image intensity and gradient/boundary cues. The fine segmentation component 226 performs an energy minimization of edge costs and derives the globally optimal bipartition of the image into one or more features, including regions of fluid volume, and background. This formulation is used to segment pathologic ocular structures by encoding edge weights according to an associated image gradient and/or neighborhood similarity metrics (i.e., a parameter representing the similarity of pixels connected to a given pixel associated with the edge) as well as a priori estimates of the pixel intensity and histogram distributions of pathologic structures.

In the illustrated implementation, segmentation is performed on a frame-by-frame basis, with frames processed sequentially according to their spatial ordering. The segmentation boundary in an adjacent frame is used to reweight edges on the current frame to produce a linearly decreasing cost function as the edges approaches the adjacent segmentation. Accordingly, the segmentation in each new frame can be guided by the results of previous frames to provide a continuous boundary for the segmented features. Adjacent frames are then combined to generate a three-dimensional polygonal mesh from the set of boundaries of interest for a given application. The generated polygonal mesh volumes can be provided to a user interface 228 to be accessible to a user at the display 218. In practice, the segmentation boundaries from the fine segmentation component 226 can represent full-thickness macular holes, macular pseudoholes, lamellar holes, vitreomacular adhesion, VMT, ERM, and choroidal thickness in the posterior segment. Of particular interest for the illustrated system 200, the segmented features can also include subretinal fluid, sub RPE fluid, intra-RPE fluid, and intraretinal fluid, as well as a total retinal volume.

Once appropriate volumes have been established, a plurality of volumetric parameters can be calculated form the polygonal mesh volumes at a volumetric measurement component 230. The specific volumetric parameters to be calculated can vary with the application and the specific segmented feature and can include, for example, a total volume, a base area, a top area, a maximal base width, and a minimum width (e.g., of a full thickness macular hole). The calculated parameters can be provided to a feature extractor 232 to generate one or more metrics indicative of retinal thickness and the prevalence of fluid within and underneath the retina within a region of interest, including, for example, the eye as a whole, the macular region, a specific retinal layer or portion of a retinal layer, retinal bands or zones, or another designated region, such as a selected subfield in the eye. In the illustrated implementation, one set of features for a given region can include various metrics that are functions of two or more volumes from the selected region, including the total retinal volume within the region of interest, $V_{ret}$, the volume of subretinal fluid within the region of interest, $V_{sub}$, and the volume of intraretinal fluid within the region of interest, $V_{int}$.

One metric that can be extracted is the dry retinal volume, defined as the difference between the total retinal volume and a sum of the intraretinal fluid volume and the subretinal fluid volume. The dry retinal volume, $V_{dry}$, can be expressed as:

$$V_{dry} = V_{tot} - (V_{sub} + V_{int}) \quad \text{Eq. 1}$$

Another metric is the total fluid index, which is defined as the ratio of the total fluid volume, that is, the sum of the intraretinal fluid volume and the subretinal fluid volume, to the total retinal volume. The total fluid index, TFI, can be expressed as:

$$TFI = \frac{(V_{sub} + V_{int})}{V_{tot}} \quad \text{Eq. 2}$$

A subretinal fluid index can be calculated as the ratio of the subretinal fluid volume to the total retinal volume. The subretinal fluid index, SFI, can be expressed as:

$$SFI = \frac{V_{sub}}{V_{tot}} \quad \text{Eq. 3}$$

An intraretinal fluid index can be calculated as the ratio of the intraretinal fluid volume to the total retinal volume. The intraretinal fluid index, IFI, can be expressed as:

$$IFI = \frac{V_{int}}{V_{tot}} \quad \text{Eq. 4}$$

A retinal fluid index can be calculated as the ratio of the intraretinal fluid volume to the difference between the total retinal volume and the subretinal volume. The retinal fluid index, RFI, can be expressed as:

$$RFI = \frac{V_{int}}{(V_{tot} - V_{sub})} \quad \text{Eq. 5}$$

An additional set of metrics, referred to herein as fluid volatility metrics, can be determined by taking a measure of deviation (e.g., range, interquartile range, standard deviation, variance, etc.) of the fluid volume or one of the fluid metrics (e.g., $V_{dry}$, TFI, SFI, IFI, or RFI) over a period of time. In one implementation, fluid volatility metrics can be used to predict the response of a patient to various therapeutic interventions, as high fluid volatility has been found by the inventors to correlate with poor tolerance of various treatments for diabetic macular edema. The trend of the volume of these metrics (e.g., as determined via a slope of a linear fit) can also be used as a predictor at the machine learning model 202.

The extracted metrics can be provided to the machine learning model 202 configured to provide a clinical parameter for a patient according to at least the extracted metrics. It will be appreciated, of course, that the machine learning model 202 may also use other predictors, in the form of biometric parameters associated with the patient, including categorical predictors, such as predictors representing biological sex, medical history, and the presence or absence of various medical conditions, as well as integral or ratio parameters, such as age, blood glucose level, blood pressure, intraocular pressure, or similar parameters.

The machine learning model 202 can utilize one or more pattern recognition algorithms, implemented, for example, as classification and regression models, each of which analyze the extracted predictors or a subset of the extracted predictors to assign a clinical parameter to the user. It will be appreciated that the clinical parameter can be categorical or continuous. For example, a categorical parameter can represent a selected intervention, a specific disorder, a degree of expected or actual disease progression, a degree of change in visual acuity, or a range of binned likelihood values for any of these categories. A continuous parameter can represent a change in a metric of visual acuity (e.g., number of letters on a visual acuity test) or a likelihood that a given patient falls within one of the categories.

The clinical parameter can be provided to a user at the display 218 or stored on the non-transitory computer readable medium 210, for example, in an electronic medical record associated with the patient. Where multiple classification and regression models are used, the machine learning model 202 can include an arbitration element can be utilized to provide a coherent result from the various algorithms. Depending on the outputs of the various models, the arbitration element can simply select a class from a model having a highest confidence, select a plurality of classes from all models meeting a threshold confidence, select a class via a voting process among the models, or assign a numerical parameter based on the outputs of the multiple models. Alternatively, the arbitration element can itself be implemented as a classification model that receives the outputs of the other models as features and generates one or more output classes for the patient.

The machine learning model 202, as well as any constituent models, can be trained on training data representing the various classes of interest. The training process of the machine learning model 202 will vary with its implementation, but training generally involves a statistical aggregation of training data into one or more parameters associated with the output classes. Any of a variety of techniques can be utilized for the models, including support vector machines, regression models, self-organized maps, fuzzy logic systems, data fusion processes, boosting and bagging methods, rule-based systems, or artificial neural networks.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. An SVM classifier utilizes a user-specified kernel function to organize training data within a defined feature space. In the most basic implementation, the kernel function can be a radial basis function, although the systems and methods described herein can utilize any of a number of linear or non-linear kernel functions.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

A regression model applies a set of weights to various functions of the extracted features, most commonly linear functions, to provide a continuous result. In general, regression features can be categorical, represented, for example, as zero or one, or continuous. In a logistic regression, the output of the model represents the log odds that the source of the extracted features is a member of a given class. In a binary classification task, these log odds can be used directly as a confidence value for class membership or converted via the logistic function to a probability of class membership given the extracted features.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used, but a continuous parameter can be computed according to a number of decisions trees that select a given task.

Figure 3:
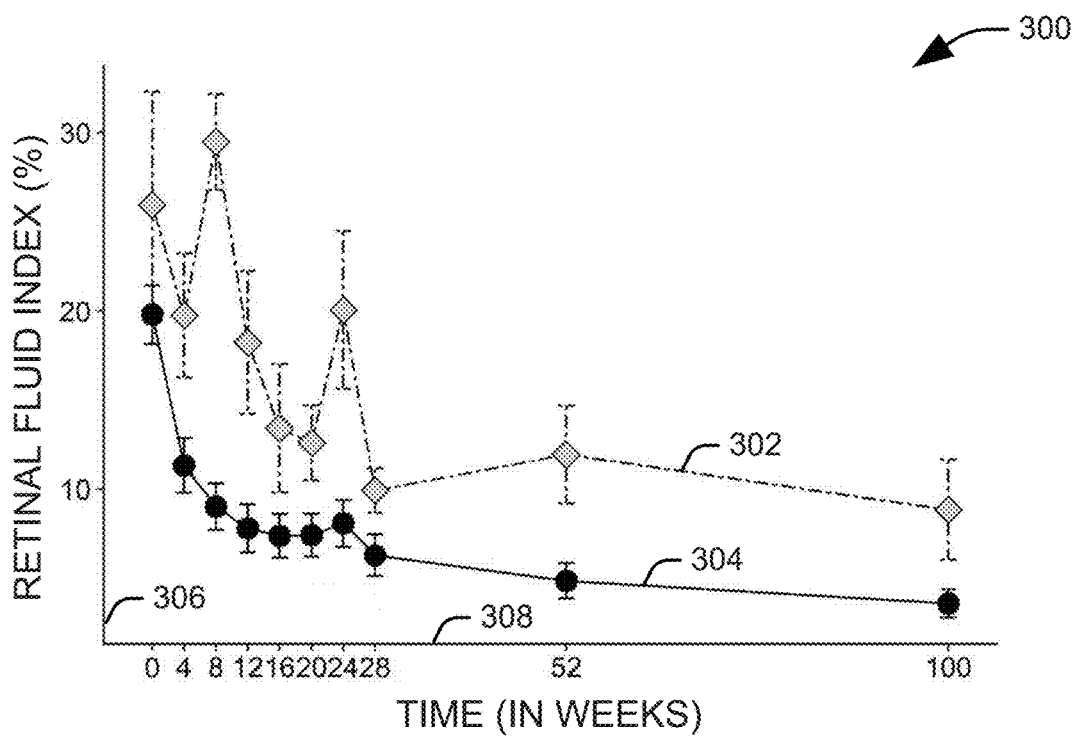
FIG. 3 illustrates a chart comparing patients having an increase in the retinal fluid index greater than five percentage points, represented as a first plot, to patients not experiencing such an increase, represented as a second plot, between the fourth and eight weeks of a 2q8 treatment regimen.

FIG. 3 illustrates a chart 300 comparing patients having an increase in the retinal fluid index greater than five percentage points, representing increased fluid volatility, represented as a first plot 302, to patients not experiencing such an increase, represented as a second plot 304, between the fourth and eight weeks of a 2q8 treatment regimen. A 2q8 treatment regime, as used herein, is a course of treatment in which an intravitreal aflibercept injection is provided every four weeks for the first sixteen weeks, and every eight weeks thereafter. The vertical axis 306 represents the average retinal fluid index across patients for a given one of the two groups, as a percentage, and the horizontal axis 308 represents the passage of time in weeks. It will be noted that the patients 302 for whom the retinal fluid index increased during the initial treatment phase also experience a spike in the retinal fluid index shortly after the transition to the less frequent injections at week 16. The patients 304 for whom the retinal fluid index remained relatively stable during the initial weeks of treatment did not experience any increase in the retinal fluid index after the transition to less frequent injections. As a result, the retinal fluid index can be an important indicator of the patient's likely response to the 2q8 regimen and can be used to identify patients for whom a 2q4 regime, in which the frequency of the injections is maintained, is a superior option.

Figure 5:
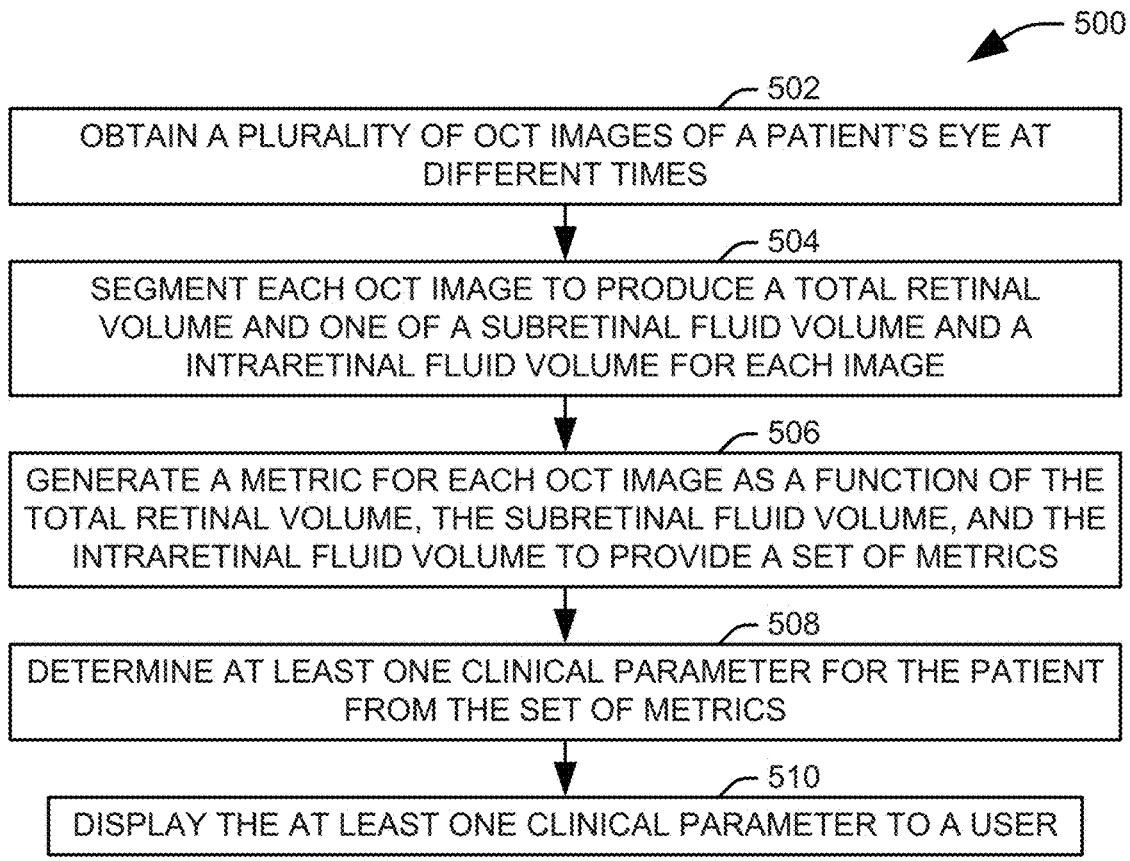
FIG. 5 illustrates another example of a method for evaluating an eye using retinal fluid volumes to provide a clinical parameter.
Figure 4:
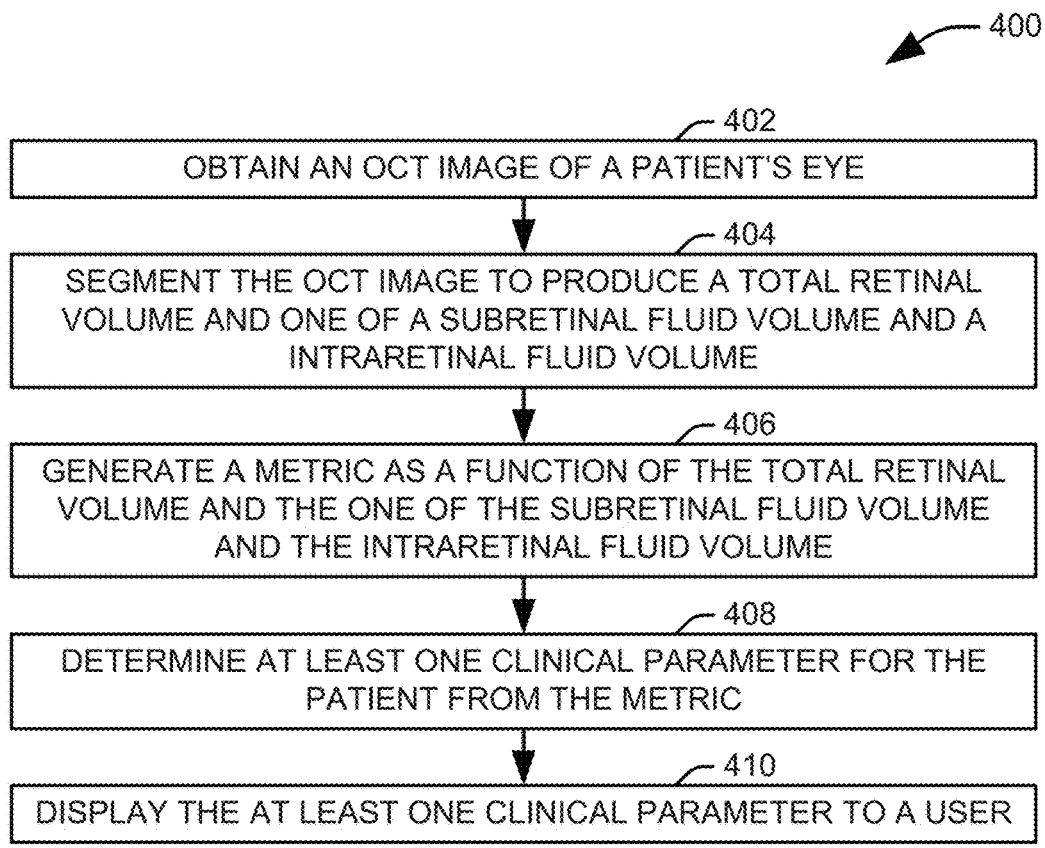
FIG. 4 illustrates one example of a method for evaluating an eye using retinal fluid volumes to provide a clinical parameter.

In view of the foregoing structural and functional features described above, methods in accordance with various aspects of the present invention will be better appreciated with reference to FIGS. 4 and 5. While, for purposes of simplicity of explanation, the methods of FIGS. 4 and 5 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect the present invention.

FIG. 4 illustrates one example of a method 400 for evaluating an eye using retinal fluid volumes to provide a clinical parameter. At 402, an optical coherence tomography (OCT) image of an eye of a patient is obtained. In one implementation, the OCT image is obtained at a spectral domain OCT (SD-OCT) imager. At 404, the OCT image is segmented to produce a total retinal volume and one of a subretinal fluid volume and an intraretinal fluid volume for a region of interest within the eye. In one implementation, all three fluid volumes can be segmented.

At 406, a metric is generated as a function of the total retinal volume and the one of the subretinal fluid volume and the intraretinal fluid volume. The metric can include, for example, any of the metrics from Equations 1-5. In one implementation, multiple metrics can be calculated over time, and a measure of deviation or trend of one of the fluid volumes or the metrics can be calculated as a metric. At 408, at least one clinical parameter for the patient is determined from the metric. In one implementation, a clinical parameter can be calculated as a function of the metric or as a change in the metric over time. In another implementation, the metric can be provided as one of a plurality of features to a machine learning model which produces the clinical parameter as a categorical or continuous parameter representing a diagnosis, a prognosis, or a response to treatment for the patient. At 410, the determined at least one clinical parameter is provided to a user at a display.

FIG. 5 illustrates another example of a method 500 for evaluating an eye using retinal fluid volumes to provide a clinical parameter. At 502, a plurality of optical coherence tomography (OCT) images of an eye of a patient are obtained, with each of the plurality of OCT images being obtained at a different time. In one example, the various images are obtained at times separated by intervals of hours or days. In one implementation, each OCT image is obtained at a spectral domain OCT (SD-OCT) imager. At 504, each of the plurality of OCT images is segmented to produce a total retinal volume, a subretinal fluid volume, and an intraretinal fluid volume for a region of interest within the eye for each OCT image. At 506, a metric is generated for each OCT image as a function of the total retinal volume, the subretinal fluid volume, and the intraretinal fluid volume to provide a set of metrics. The metric can include, for example, any of the dry retinal volume of Equation 1, the total fluid index of Equation 2, and the retinal fluid index of Equation 5. In one implementation, multiple metrics can be calculated over time, and a measure of deviation or trend of one of the fluid volumes or the metrics can be calculated as a metric.

At 508, at least one clinical parameter for the patient is determined from the set of metrics. In one implementation, a clinical parameter can be calculated as a function of the metric or as a change in the metric over time. In another implementation, the metric can be provided as one of a plurality of features to a machine learning model which produces the clinical parameter as a categorical or continuous parameter representing a diagnosis, a prognosis, or a response to treatment for the patient. At 510, the determined at least one clinical parameter is provided to a user at a display.

Figure 6:
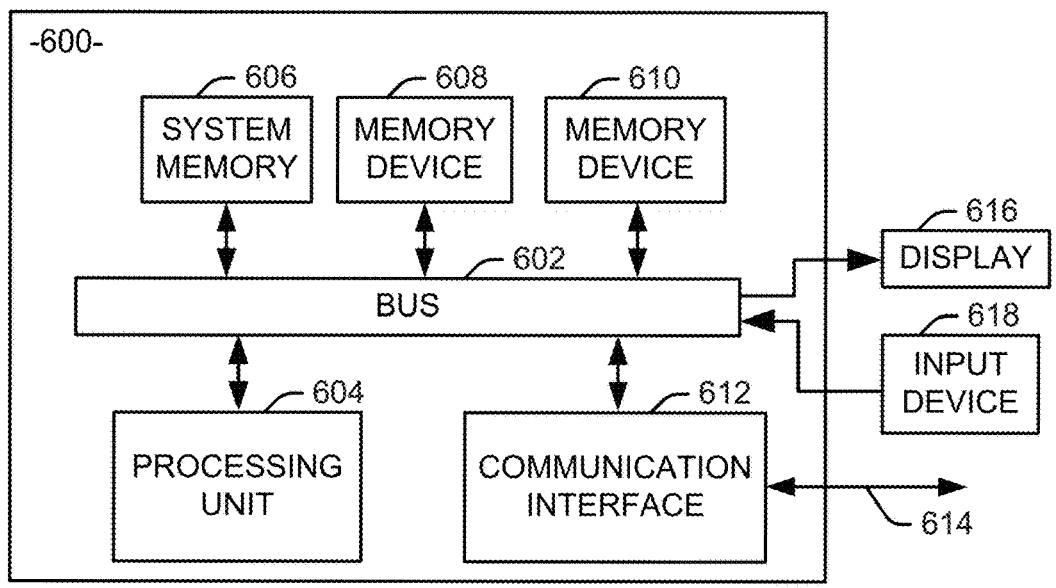
FIG. 6 is a schematic block diagram illustrating an exemplary system of hardware components capable of implementing examples of the systems and methods disclosed herein.

FIG. 6 is a schematic block diagram illustrating an exemplary system 600 of hardware components capable of implementing examples of the systems and methods disclosed in FIGS. 1-5. The system 600 can include various systems and subsystems. The system 600 can be a personal computer, a laptop computer, a workstation, a computer system, an appliance, an application-specific integrated circuit (ASIC), a server, a server blade center, a server farm, etc.

The system 600 can includes a system bus 602, a processing unit 604, a system memory 606, memory devices 608 and 610, a communication interface 612 (e.g., a network interface), a communication link 614, a display 616 (e.g., a video screen), and an input device 618 (e.g., a keyboard and/or a mouse). The system bus 602 can be in communication with the processing unit 604 and the system memory 606. The additional memory devices 608 and 610, such as a hard disk drive, server, stand-alone database, or other non-volatile memory, can also be in communication with the system bus 602. The system bus 602 interconnects the processing unit 604, the memory devices 606-610, the communication interface 612, the display 616, and the input device 618. In some examples, the system bus 602 also interconnects an additional port (not shown), such as a universal serial bus (USB) port.

The processing unit 604 can be a computing device and can include an application-specific integrated circuit (ASIC). The processing unit 604 executes a set of instructions to implement the operations of examples disclosed herein. The processing unit can include a processing core. The additional memory devices 606, 608 and 610 can store data, programs, instructions, database queries in text or compiled form, and any other information that can be needed to operate a computer. The memories 606, 608 and 610 can be implemented as computer-readable media (integrated or removable) such as a memory card, disk drive, compact disk (CD), or server accessible over a network. In certain examples, the memories 606, 608 and 610 can comprise text, images, video, and/or audio, portions of which can be available in formats comprehensible to human beings. Additionally or alternatively, the system 600 can access an external data source or query source through the communication interface 612, which can communicate with the system bus 602 and the communication link 614.

In operation, the system 600 can be used to implement one or more parts of a diagnostic imaging system in accordance with the present invention. Computer executable logic for implementing the diagnostic imaging system resides on one or more of the system memory 606, and the memory devices 608, 610 in accordance with certain examples. The processing unit 604 executes one or more computer executable instructions originating from the system memory 606 and the memory devices 608 and 610. The term "computer readable medium" as used herein refers to a medium that participates in providing instructions to the processing unit 604 for execution.

From the above description of the invention, those skilled in the art will perceive improvements, changes, and modifications. Such improvements, changes, and modifications within the skill of the art are intended to be covered by the appended claims.

Having described the invention, we claim:

1. A method comprising:
obtaining an optical coherence tomography (OCT) image of an eye of a patient;
segmenting the OCT image to produce a total retinal volume and one of a subretinal fluid volume and an intraretinal fluid volume for a region of interest within the eye;
generating a metric as a function of the total retinal volume and the one of the subretinal fluid volume and the intraretinal fluid volume;
determining at least one clinical parameter for the patient from the metric; and
providing the determined at least one clinical parameter to a user at a display.

2. The method of claim 1, wherein segmenting the OCT image comprises segmenting the OCT image to produce the total retinal volume and the subretinal fluid volume, and a intraretinal fluid volume, and generating the metric comprises generating the metric as a function of the total retinal volume, the intraretinal fluid volume, and the subretinal fluid volume.

3. The method of claim 2, wherein generating the metric as a function of the total retinal volume, the intraretinal fluid volume, and the subretinal fluid volume comprises generating a dry retinal volume metric represented as the difference between the total retinal volume and the sum of the subretinal fluid volume and the intraretinal fluid volume.

4. The method of claim 2, wherein generating the metric as a function of the total retinal volume, the intraretinal fluid volume, and the subretinal fluid volume comprises generating a total fluid index as a ratio of the sum of the subretinal fluid volume and the intraretinal fluid volume to the total retinal volume.

5. The method of claim 2, wherein generating the metric as a function of the total retinal volume, the intraretinal fluid volume, and the subretinal fluid volume comprises generating a retinal fluid index as a ratio of the intraretinal fluid volume to the difference between the total retinal volume and the subretinal fluid volume.

6. The method of claim 1, wherein segmenting the OCT image comprises segmenting the OCT image to produce the total retinal volume and the subretinal fluid volume and generating the metric comprises generating a subretinal fluid index as a ratio of the subretinal fluid volume to the total retinal volume.

7. The method of claim 1, wherein segmenting the OCT image comprises segmenting the OCT image to produce the total retinal volume and the intraretinal fluid volume and generating the metric comprises generating an intraretinal fluid index as a ratio of the intraretinal fluid volume to the total retinal volume.

8. The method of claim 1, wherein obtaining the OCT image of the eye of the patient comprises obtaining a first OCT image at a first time, segmenting the OCT image comprises segmenting the first OCT image to produce a first total retinal volume and a first subretinal fluid volume, generating the metric comprises generating a first metric as a function of the first total retinal volume and the first subretinal fluid volume, and the method further comprises:

obtaining a second OCT image of the eye of the patient at a second time;

segmenting the second OCT image to provide a second fluid volumes and a second total retinal volumes; and generating a second metric as a function of the second total retinal volume and the second subretinal fluid volume;

wherein determining the at least one clinical parameter comprises determining a clinical parameter from the first metric and the second metric.

9. The method of claim 8, wherein determining the clinical parameter from the first metric and the second metric comprises calculating a measure of deviation across at least the first metric and the second metric.

10. The method of claim 8, wherein determining the clinical parameter from the first metric and the second metric comprises calculating a trend, representing the change over time from the first metric to the second metric.

11. The method of claim 1, wherein determining at least one clinical parameter for the patient from the metric comprises providing the metric as a predictor to a machine learning model.

12. A system comprising:
a processor; and
a non-transitory computer readable medium storing executable instructions executable by the processor, the executable instructions comprising:
an imager interface that receives an optical coherence tomography (OCT) image of an eye of a patient;
a segmentation component that segments the OCT image to produce a total retinal volume and one of an intraretinal volume and a subretinal fluid volume for a region of interest within the eye;
a feature extractor that generates a metric as a function of the total retinal volume and the one of the intraretinal volume and the subretinal fluid volume; and
a machine learning model that determines at least one clinical parameter for the patient from the metric.

13. The system of claim 12, wherein the feature extractor extracts at least one biometric parameter from an electronic health records database, and the machine learning model determines the at least one clinical parameter for the patient from the metric and the biometric parameter.

14. The system of claim 12, further comprising a spectral domain optical coherence tomography imager that provides the OCT image to the imager interface.

15. The system of claim 12, further comprising a display and the executable instructions further comprising a user interface that provides the at least one clinical parameter to the display.

16. The system of claim 12, wherein the region of interest is the macular region of the eye.

17. The system of claim 12, wherein the segmentation component segments the OCT image to produce the total retinal volume, the intraretinal volume, and the subretinal fluid volume for the region of interest, and the feature extractor generates the metric as a function of the total retinal volume, the intraretinal volume, and the subretinal fluid volume.

18. A method comprising:
obtaining a plurality of optical coherence tomography (OCT) images of an eye of a patient, each of the plurality of OCT images being taken at a different time
segmenting each of the plurality of OCT images to produce each of a total retinal volume, a subretinal fluid volume, and an intraretinal fluid volume for a region of interest within the eye for each of the plurality of OCT images;
generating, for each of the plurality of OCT images, a metric as a function of the total retinal volume, the subretinal fluid volume, and the intraretinal fluid volume to provide a set of metrics;
determining at least one clinical parameter for the patient from the set of metrics; and
providing the determined at least one clinical parameter to a user at a display.

19. The method of claim 18, wherein generating the metric for each of the plurality of OCT images comprises generating a retinal fluid index as a ratio of the intraretinal fluid volume to the difference between the total retinal volume and the subretinal fluid volume.

20. The method of claim 19, further comprising generating a measure of deviation for the retinal fluid index across the plurality of OCT images, wherein determining the at least one clinical parameter for the patient from the set of metrics comprises determining the at least one clinical parameter for the patient from the measure of deviation for the retinal fluid index.

* * * * *